United States Patent
Liemersdorf et al.

(10) Patent No.: US 8,940,144 B2
(45) Date of Patent: Jan. 27, 2015

(54) SENSOR ELEMENT AND METHOD FOR DETERMINING GAS COMPONENTS IN GAS MIXTURES, AND USE THEREOF

(75) Inventors: Dirk Liemersdorf, Gerlingen (DE); Thomas Classen, Stuttgart (DE); Benjamin Sillmann, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 941 days.

(21) Appl. No.: 13/003,487

(22) PCT Filed: Jun. 25, 2009

(86) PCT No.: PCT/EP2009/057935
§ 371 (c)(1),
(2), (4) Date: Apr. 13, 2011

(87) PCT Pub. No.: WO2010/003826
PCT Pub. Date: Jan. 14, 2010

(65) Prior Publication Data
US 2011/0314898 A1    Dec. 29, 2011

(30) Foreign Application Priority Data

Jul. 10, 2008 (DE) .......................... 10 2008 040 314
Dec. 5, 2008 (DE) .......................... 10 2008 044 374

(51) Int. Cl.
G01N 27/419    (2006.01)

(52) U.S. Cl.
CPC .................................. *G01N 27/419* (2013.01)
USPC ........................................ 204/426; 204/424

(58) Field of Classification Search
USPC ................................................ 204/424, 426
See application file for complete search history.

(56) References Cited

U.S. PATENT DOCUMENTS

| 4,724,061 | A | * | 2/1988 | Nyberg | .......................... 204/412 |
| 4,834,051 | A | * | 5/1989 | Tanaka et al. | ................. 123/703 |
| 4,909,922 | A | | 3/1990 | Kato et al. | |
| 5,360,528 | A | * | 11/1994 | Oh et al. | ........................ 204/425 |
| 5,686,654 | A | * | 11/1997 | Friese et al. | ................. 73/23.32 |
| 6,093,294 | A | * | 7/2000 | Kato et al. | .................... 204/425 |
| 6,136,170 | A | * | 10/2000 | Inoue et al. | ................... 204/424 |
| 6,936,149 | B2 | | 8/2005 | Wahl et al. | |

(Continued)

FOREIGN PATENT DOCUMENTS

| DE | 39 17 710 | 1/1990 |
| DE | 199 32 048 | 1/2001 |

(Continued)

OTHER PUBLICATIONS

International Search Report, PCT International Patent Application No. PCT/EP2009/057935, dated Dec. 9, 2009.

*Primary Examiner* — Lisa Caputo
*Assistant Examiner* — Punam Roy
(74) *Attorney, Agent, or Firm* — Kenyon & Kenyon LLP

(57) ABSTRACT

A sensor element of a gas sensor for determining gas components in gas mixtures, having at least one electrochemical measuring cell which is formed by a ceramic substrate and electrodes placed thereon. The sensor element includes at least one interior chamber which is sealed in a gas-tight manner, in which at least one first internal electrode is positioned, which forms an electrochemical cell with each of a second and an additional electrode of the sensor element, one of the electrochemical cells being an electrochemical pump cell, and the second or other electrode being exposed to the measuring gas.

14 Claims, 7 Drawing Sheets

(56) References Cited

U.S. PATENT DOCUMENTS

| | | | |
|---|---|---|---|
| 6,942,772 B1 | 9/2005 | Schneider et al. | |
| 7,922,884 B2 * | 4/2011 | Strohmaier et al. | 204/424 |
| 2002/0162755 A1 * | 11/2002 | Kato et al. | 205/781 |
| 2003/0183520 A1 * | 10/2003 | Mabuchi et al. | 204/424 |
| 2004/0112765 A1 * | 6/2004 | Alkemade et al. | 205/784 |
| 2004/0231985 A1 * | 11/2004 | Kato et al. | 204/426 |
| 2005/0000832 A1 * | 1/2005 | Holoch et al. | 205/782 |
| 2005/0252771 A1 * | 11/2005 | Wiedenmann et al. | 204/426 |
| 2009/0038941 A1 | 2/2009 | Stahl et al. | |
| 2009/0107839 A1 | 4/2009 | Scheffel et al. | |
| 2009/0114539 A1 * | 5/2009 | Ziegler et al. | 204/424 |
| 2009/0120073 A1 * | 5/2009 | Fujita et al. | 60/295 |
| 2010/0230297 A1 * | 9/2010 | Wahl et al. | 205/781 |
| 2012/0006692 A1 * | 1/2012 | Liemersdorf et al. | 205/784 |
| 2013/0081448 A1 * | 4/2013 | Bevot et al. | 73/30.04 |

FOREIGN PATENT DOCUMENTS

| | | | | |
|---|---|---|---|---|
| DE | 101 15 872 | | 10/2002 | |
| DE | 10 2004 042027 | | 3/2006 | |
| DE | 10 2005 049 775 | | 4/2007 | |
| DE | 10 2006 014681 | | 10/2007 | |
| DE | 102007049716 A1 | * | 7/2008 | ........... G01N 27/419 |
| DE | 10 2007 050 119 | | 4/2009 | |
| EP | 1 359 411 | | 11/2003 | |
| EP | 1 635 171 | | 3/2006 | |
| EP | 1 739 416 | | 1/2007 | |
| JP | 3-120456 | | 5/1991 | |
| JP | 5-180798 | | 7/1993 | |
| JP | 7-159373 | | 6/1995 | |
| JP | 2001-296272 | | 10/2001 | |
| JP | 2005-530133 | | 10/2005 | |
| WO | WO 93/21521 | | 10/1993 | |
| WO | WO 9914586 A1 | * | 3/1999 | ........... G01N 27/407 |
| WO | WO 2008080732 A1 | * | 7/2008 | |

* cited by examiner

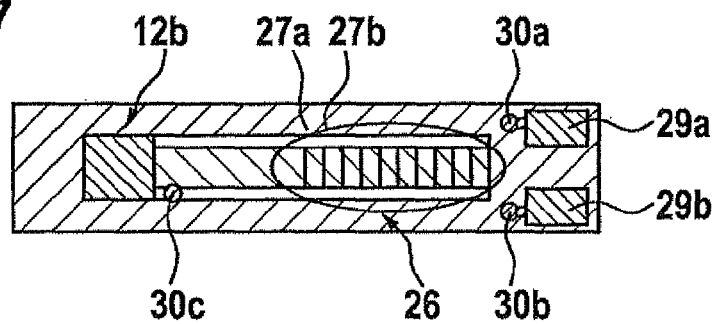
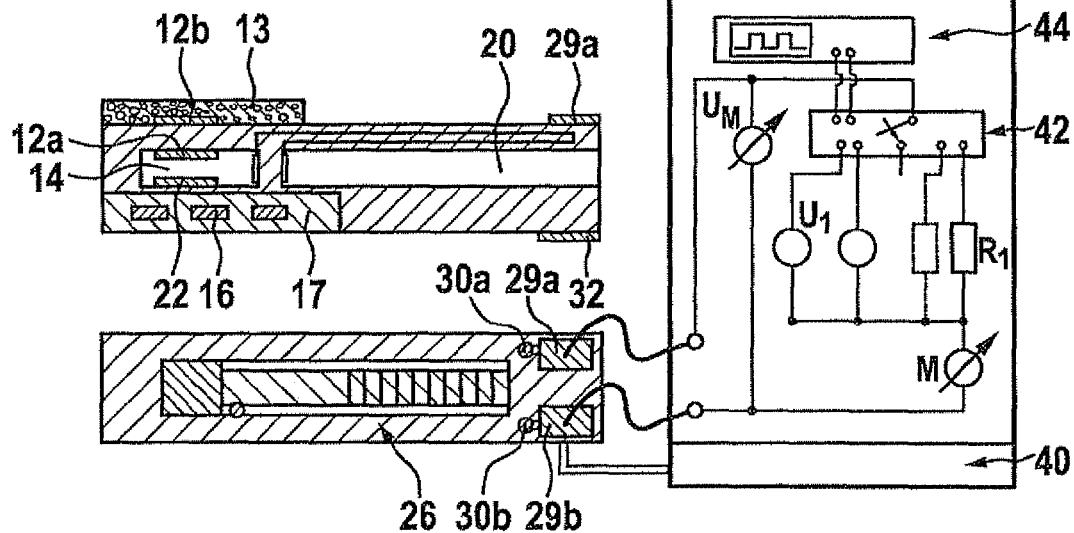
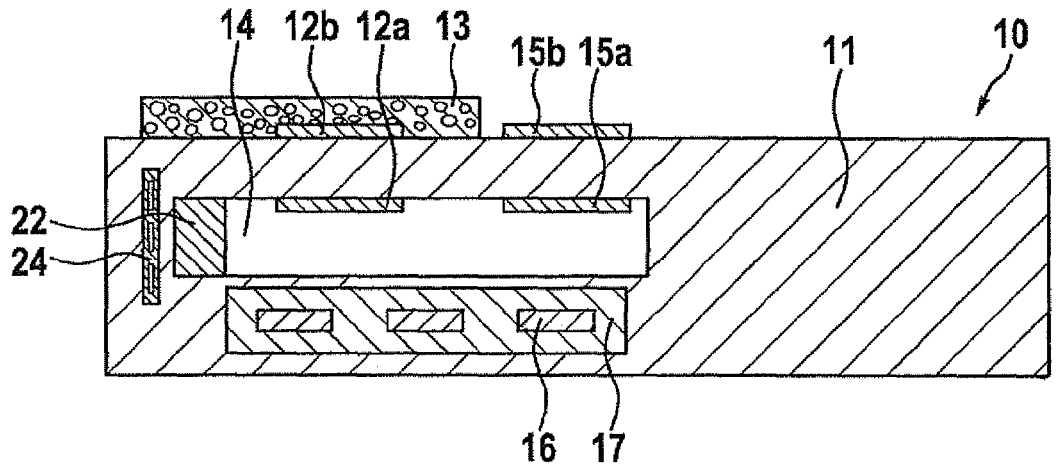

SENSOR ELEMENT AND METHOD FOR DETERMINING GAS COMPONENTS IN GAS MIXTURES, AND USE THEREOF

FIELD OF THE INVENTION

The present invention relates to a sensor element and to a method for determining gas components in gas mixtures and to the use thereof.

BACKGROUND INFORMATION

In the course of ongoing environmental legislation, there is a growing need for sensors which are able to assist in determining even very small quantities of pollutants reliably. A large role is played here in particular by measuring methods which make it possible to determine the presence of gaseous pollutants in the ppm range. In this connection, however, it is particularly challenging to determine the content of nitrogen oxides in combustion exhaust gases, due to the high proportion of oxygen which is also present. This has significance for possible utilization as OBD sensors to fulfill coming exhaust gas legislation, because in this context nitrogen oxide limits, for example, will be prescribed which are below the resolution limit of currently available solid electrolyte gas sensors.

In order to make proper allowance for these problems, a storage device for a sensor element for qualitative or quantitative determination in particular of nitrogen oxides in a gas mixture is described, for example, in German Patent Application No. DE 10 2007 050 119 A. The storage device described therein, or the sensor element containing such a storage device, is based on the idea of accumulating gas components to be determined which are present in only a low concentration in a gas mixture being analyzed, over a certain time period. To that end, a storage device which is resistant to contamination and temperature changes is provided within the sensor element.

The determination of the gas component to be detected takes place discontinuously, the gas component to be determined first being stored in a storage medium during a collecting phase and the storage state of this storage medium being detected. In a subsequent regeneration phase, the stored gas component which is to be detected is then removed again from the storage medium, for example by raising the temperature. Alternatively, the gas component to be detected which is released during the regeneration phase may be detected and its concentration ascertained.

In addition, a sensor for determining gas components in gas mixtures is described in European Patent No. EP 1 739 416 A2, which may be used among other things for determining nitrogen oxides. The described gas sensor includes a plurality of electrochemical cells and a chamber having limited inflow, which contains a reference gas atmosphere as the reference point for determining the gas component which is to be detected. In this chamber having limited inflow there are internal electrodes of electrochemical cells, with the aid of which the content of gas components which are to be detected may be determined by voltametric means.

SUMMARY

An object of the present invention is to provide a sensor element and a method for determining gas components in gas mixtures which make it possible to determine low concentration gas components in a gas mixture alongside larger quantities of oxygen, for example.

According to the present invention, a quantity of oxygen equivalent to the gas component to be determined is accumulated in a gas-tight sealed interior chamber of the sensor element. This is followed by removing the accumulated oxygen by applying a pump voltage to an electrochemical pump cell of the sensor element, during which process the oxygen is removed from the gas-tight sealed interior chamber of the sensor element.

The particular advantage of this procedural approach is that by accumulating a quantity of oxygen equivalent to the quantity of the gas component to be determined, a greater absolute quantity of a gas equivalent to the gas component to be detected is generated, so that the measuring accuracy is significantly improved because of a more favorable signal-to-noise ratio.

Contrary to the conventional approach, in the present case it is not the gas component to be detected itself which is accumulated, but rather a quantity of oxygen equivalent thereto. This has the advantage that oxygen is significantly more stable thermodynamically than gas components of lower concentration, such as nitrogen oxides, hydrocarbons, or ammonia. In this way, and also due to the spatial separation of the accumulation zone for the gas mixture to be determined, the risk that a certain part of the gas component to be detected will be lost during the accumulation phase through abreaction is minimized. For a definitive measurement of the gas quantity, the entire quantity of accumulated gas is thus available for a determination.

It is advantageous if a quantity of oxygen equivalent to the quantity of gas component to be detected is accumulated using an electrochemical pump cell, one of whose electrodes is exposed to the gas mixture to be detected and whose other electrode is exposed to an interior gas-tight sealed chamber of the sensor element.

In this way, a defined transport of oxygen ions through solid electrolyte layers of the sensor element into the interior gas-tight sealed chamber of the sensor element may be ensured. According to a particularly simple specific embodiment, the electrodes of this electrochemical pump cell are connected to each other through a trimmable resistor.

This specific embodiment makes it possible to operate the electrochemical pump cell as a so-called autonomous pump cell. In this case it is not necessary to apply a pump voltage to the electrochemical pump cell externally. Instead, the pump voltage results from differences in concentration between the gas mixture to be detected and the gas atmosphere existing in the interior gas-tight chamber of the sensor element.

The level of this pump activity may be set by trimming the ohmic resistor through which the two pump electrodes of the electrochemical pump cell are short circuited. By not applying an external pump voltage to the electrodes of the electrochemical pump cell a simplified sensor layout results, since it is possible to dispense with external contacting of the electrodes.

It is also advantageous if the pump electrode of the electrochemical pump cell which is exposed to the gas mixture to be detected is designed as a so-called mixed-potential electrode. The concept of a mixed-potential electrode means that it has limited catalytic activity, so that—in contrast to catalytically active electrodes such as platinum electrodes—gas components of a gas mixture do not react with each other while arriving at the state of thermodynamic equilibrium. Instead, the material of the mixed-potential electrode results in setting of thermodynamic equilibrium being kinetically inhibited.

Hence it is possible, for example, to detect reducible gas components of a gas mixture in addition to other gas components, for example oxidizable gas components of a gas mixture. In contrast, when a catalytically active electrode is used it would only be possible to detect reaction products of the two gases, such as water or carbon monoxide.

According to another advantageous specific embodiment, a layer of an oxygen-storing material, for example a ceramic material, is provided inside the described gas-tight sealed interior chamber of the sensor element.

The advantage of this specific embodiment is that during a collecting phase oxygen is continuously pumped electrochemically into a gas-tight sealed interior chamber of the sensor element. A rise in pressure or an increase in the oxygen concentration may be expected in this process, depending on the dimensioning of the interior chamber. This results directly in a reduction of the pumping performance of the electrochemical pump cell involved in transporting the oxygen into the gas-tight sealed interior chamber of the sensor element. But if a material which stores oxygen is provided in the interior of the gas-tight sealed interior chamber of the sensor element, this material absorbs the oxygen transported into the interior of the gas-tight sealed interior chamber, and this oxygen is available in absorbed form for a determination.

According to one particularly advantageous specific embodiment, in this case an additional heating element is provided, which is positioned in the area of the aforementioned layer of an oxygen-absorbing ceramic material, so that this layer is warmed during the measuring process and gives off the stored oxygen to the gas phase of the gas-tight sealed interior chamber of the sensor element for measurement. Large quantities of oxygen may be accumulated in this way, so that a particularly accurate sensor signal of the sensor element results.

Another advantageous measure for improving the measuring accuracy of the described sensor element includes providing another interior gas chamber within the sensor element in the form of a measuring gas chamber, which is in fluid-conducting contact with the gas mixture to be determined, an electrode of an additional electrochemical cell of the sensor element being provided in this measuring gas chamber, which catalytically decomposes the molecular oxygen contained in the gas mixture.

In this way, the oxygen contained in the gas mixture may be removed selectively from the gas being measured, without the gas component to be detected being broken down. The concentration ratio of the component to be detected to oxygen contained in the gas mixture is improved in this way, so that a lower cross-sensitivity to oxygen results.

BRIEF DESCRIPTION OF THE DRAWINGS

Exemplary embodiments of the present invention are illustrated in the figures and explained in greater detail below.

FIG. 7 shows a top view of the sensor element depicted in FIG. 6.

FIG. 8 shows a schematic longitudinal section of a sensor element according to a fifth variant of the sensor element depicted in FIG. 1, as well as a top view and a schematic depiction of the wiring thereof.

FIG. 9 shows a schematic longitudinal section of a sensor element according to a second specific embodiment of the present invention.

DETAILED DESCRIPTION OF EXAMPLE EMBODIMENTS

Figure 1:
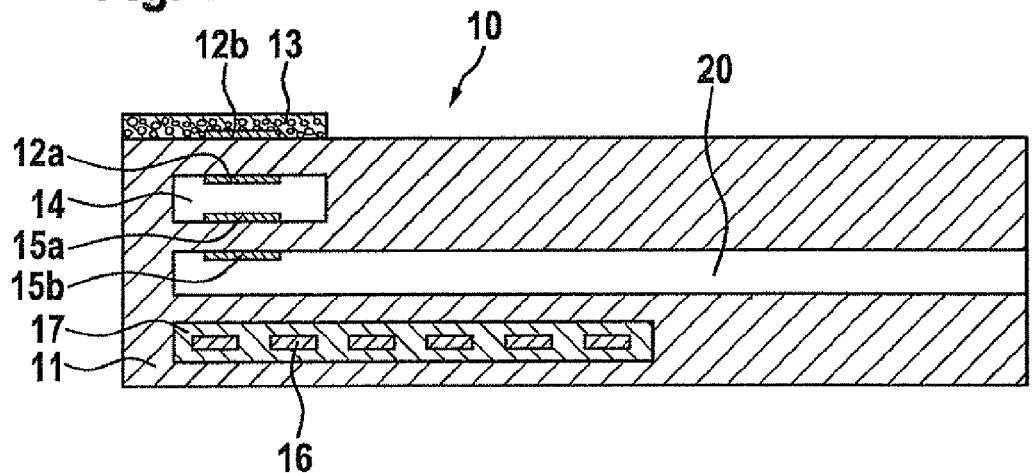
FIG. 1 shows a schematic longitudinal section through a first specific embodiment of the present invention.

FIG. 1 depicts, by way of example, a sensor element according to a first specific embodiment of the present invention. Sensor element 10 includes, for example, a ceramic sensor body 11, which is preferably formed of a plurality of solid electrolyte layers. An example of the solid electrolyte used is zirconium dioxide stabilized or partially stabilized with yttrium oxide.

The integrated form of the planar ceramic body of sensor element 10 is produced in this case by laminating together ceramic films imprinted with functional layers, followed by sintering the laminated structure.

Sensor element 10 has a gas-tight sealed interior chamber 14. The latter is preferably not in fluid-conducting contact with a gas mixture to be determined, nor with a reference gas atmosphere or the ambient air.

In interior chamber 14 there is a first internal pump electrode 12$a$, which together with a first external pump electrode 12$b$ forms an electrochemical pump cell. An electrochemical pump cell in this case means a system of at least two electrodes in contact with a solid electrolyte layer, these electrodes serving to transport oxygen ions electrochemically through the named solid electrolyte layer due to application of a pump voltage.

First external pump electrode 12$b$ is positioned, for example, on a large surface of sensor element 10, in contact with a gas mixture which is to be determined. To protect first external pump electrode 12$b$, the latter is preferably provided with a porous protective layer 13. First external pump electrode 12b is made, for example, of a catalytically active material such as platinum, palladium, iridium, tantalum or alloys thereof, or includes a mixed-potential electrode material which is at least partially catalytically inactive, such as gold, silver, copper or zinc or alloys thereof.

Sensor element 10 also includes a reference gas channel 20 which is in contact with a reference gas atmosphere, which may be formed, for example, by the air atmosphere. Positioned in reference gas channel 20 is, for example, a second external pump electrode 15b, which together with a second internal pump electrode 15a positioned in interior chamber 14 forms a second electrochemical pump cell.

To enable sensor element 10 to be heated to an operating temperature of, for example, 400° C. to 1000° C., sensor element 10 also has a heating element 16 which is surrounded, for example, by a layer 17 of a ceramic, electrically insulating material such as aluminum oxide.

Figure 2:
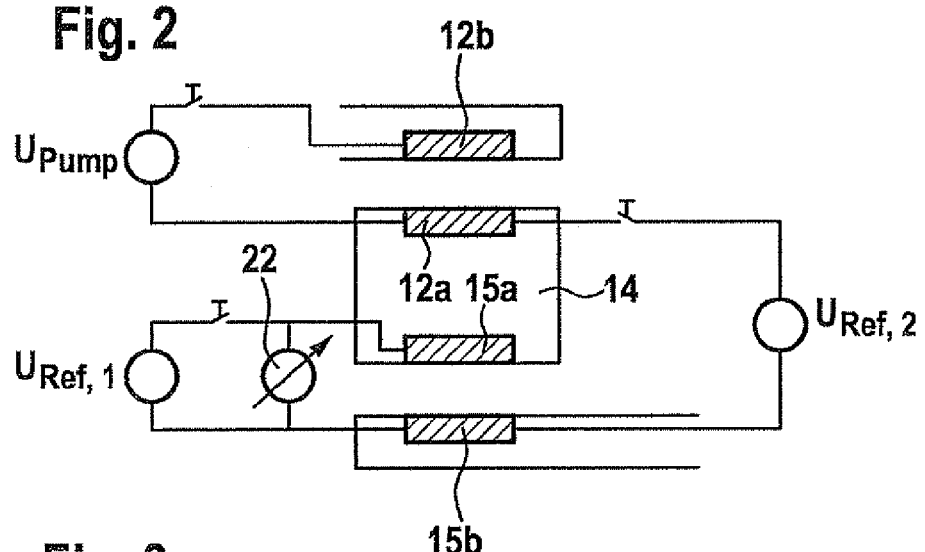
FIG. 2 shows a schematic depiction of the wiring of a sensor element according to the first specific embodiment depicted in FIG. 1.

The wiring of the sensor element shown in FIG. 1 is depicted in an exemplary specific embodiment in FIG. 2. In this case sensor element 10 is operated for example in an alternating operating mode, in which an accumulation phase and an initialization phase can be distinguished. During the accumulation phase, using first electrochemical pump cell 12a, 12b when determining reducible gas components of a gas mixture, such as oxygen, sulfur oxides or nitrogen oxides, a quantity of oxygen equivalent to a gas component to be determined is admitted into first interior chamber 14 of sensor element 10. When determining oxidizable gas components of a gas mixture, such as hydrogen, hydrocarbons or ammonia, oxygen is instead electrochemically removed from first interior chamber 14.

To that end, a pump voltage $U_{pump}$ is applied for example to pump electrodes 12a, 12b of the first electrical pump cell, which is measured in such a way that an electrochemical decomposition of the gas component to be detected occurs at the surface of first external electrode 12b, accompanied by a release of oxygen in the case of reducible gas components or an absorption of oxygen in the case of oxidizable gas components.

The released oxygen is converted to oxide ions at the electrode surface of first external pump electrode 12b, and is transported by solid electrode body 11 of sensor element 10 to first internal pump electrode 12a. There, molecular oxygen is electrochemically reconstituted. It accumulates in interior chamber 14. According to a first variant of the method, the accumulation phase may be provided for a fixed time period t.

In the subsequent measuring phase, oxygen is then transported electrochemically from first interior chamber 14, for example into reference gas channel 20. This is preferably done using second electrochemical pump cell 15a, 15b. In this process, molecular oxygen which has accumulated in interior chamber 14 is converted electrochemically to oxide ions at the surface of second internal pump electrode 15a and is transported through solid electrolyte body 11 of sensor element 10, in the course of which molecular oxygen is reconstituted at the electrode surface of second external pump electrode 15b. For this purpose an appropriate pump voltage $U_{ref,1}$ is applied to second electrochemical pump cell 15a, 15b.

At the same time, the pump current passing between the electrodes of second electrochemical pump cell 15a, 15b or the transferred charge quantity is determined, for example using an ammeter 22. These represent a measure of the absolute quantity of the molecular oxygen which has accumulated in interior chamber 14, and thus at the same time a measure of the absolute quantity of the corresponding gas component to be determined. An alternative measuring methodology consists of detecting a Nernst voltage applied to the electrodes of second electrochemical pump cell 15a, 15b. In that case time interval is detected which elapses from the beginning of the accumulation until a predefined Nernst voltage has been reached at the electrodes of the second pump cell. This time interval also correlates with a predefined absolute quantity of the gas component to be determined.

It is thus possible, through the intermediate step of an accumulation phase, to determine the absolute content of the gas component to be detected which reaches the sensitive zone of sensor element 10 within the accumulation phase. This makes it possible to also determine gas components which are present only in very low concentrations in a gas mixture which is to be determined.

If, in addition, first internal pump electrode 12a is connected to second external pump electrode 15b during the measuring phase to form an additional electrochemical pump cell, then it is possible, for example during the measuring phase, to effect an additional transport of accumulated oxygen from first chamber 14 into reference gas channel 20 by applying an appropriate pump voltage $U_{ref,2}$, which corresponds for example to the pump voltage $U_{ref,1}$ applied to the electrodes of second electrochemical pump cell 15a, 15b in the measuring phase.

This accelerates the removal of the molecular oxygen which has accumulated in interior chamber 14 during the accumulation phase. The acceleration of this process is generally based on a larger total electrode surface formed by the electrode surfaces of first and second internal pump electrodes 12a, 15a. At the same time, an oxygen partial pressure which is essentially comparable in all areas develops in interior chamber 14. A short duration of the measuring phase is desirable, since during this phase the sensor element is essentially blind and does not detect any other change in the concentration of the gas component to be detected in the gas mixture to be determined. A short measuring phase thus advantageously shortens the measuring cycle which includes the accumulation phase and the measuring phase without a loss of measuring accuracy.

However, the proposed circuitry, forming an additional electrochemical pump cell 12a, 15b, also makes it possible to set different oxygen partial pressures in different sub-areas of interior chamber 14. If $U_{ref,2}$ is chosen so that it differs from $U_{ref,1}$, an oxygen concentration gradient develops within interior chamber 14. Because of this definitely non-homogeneous distribution of the oxygen content within interior chamber 14, individual measuring properties of sensor element 10 may be manifested independently of each other.

In this way, it is possible for example to influence the correlation between first internal pump electrode 12a and the state of interior chamber 14 determined using the second internal pump electrode, by intentionally choosing different gas compositions in the area of first and second internal pump electrodes 12a, 15a, so that the ratio of the quantity of gas accumulated in the area of first and second internal pump electrodes 12a, 15a and the chamber volume of interior chamber 14 may be influenced. This wiring also makes it possible to influence the pumping process which occurs during the accumulation phase between the electrodes of first electrochemical pump cell 12a, 12b, in particular already in the initial state.

By choosing pump voltage $U_{ref,1}$ appropriately, it is possible to preselect the oxygen partial pressure which should prevail as the starting point for a subsequent accumulation phase within interior chamber 14. In this way, influence is exerted on the time period which is needed to accumulate a certain quantity of oxygen in interior chamber 14.

In addition, influence may be exerted during the initialization phase on the behavior of first electrochemical pump cell 12a, 12b by choosing an appropriate pump voltage $U_{ref,2}$.

During the initialization phase, the pump voltage $U_{ref,2}$ applied to additional electrochemical pump cell 12a, 15b may be chosen differently depending on the operating mode. Thus it is possible for example to keep $U_{ref,2}$ constant during the initialization phase. In this way the state and properties, or the initial state, of first electrochemical pump cell 12a, 12h may be influenced selectively.

According to another variant, pump voltage $U_{ref,2}$ applied to additional electrochemical pump cell 12a, 15b is chosen during the initialization phase so that pump voltage $U_{pump}$ applied to first electrochemical pump cell 12a, 12b assumes a defined value during the initialization phase, which corresponds for example to an initial value of an accumulation phase which follows the initialization phase. The advantage of this operating mode is that, for example, the accumulation may be started independently of the composition of the gas mixture to be determined, under comparable starting conditions.

Another, third variant includes choosing the pump voltage $U_{ref,2}$ applied to additional electrochemical pump cell 12a, 15h, for example during the initialization phase, so that a potential difference, which is constant in particular, occurs between first internal pump electrode 12a and another electrode which is not assignable to first or second electrochemical pump cell 12a, 12b or 15a, 15b. The advantage of this operating mode is that the control relationship is not defined by the potential of first external pump electrode 12b, which depends on the gas component to be determined, but rather for example by the oxygen-dependent potential of another electrode.

Figure 3:
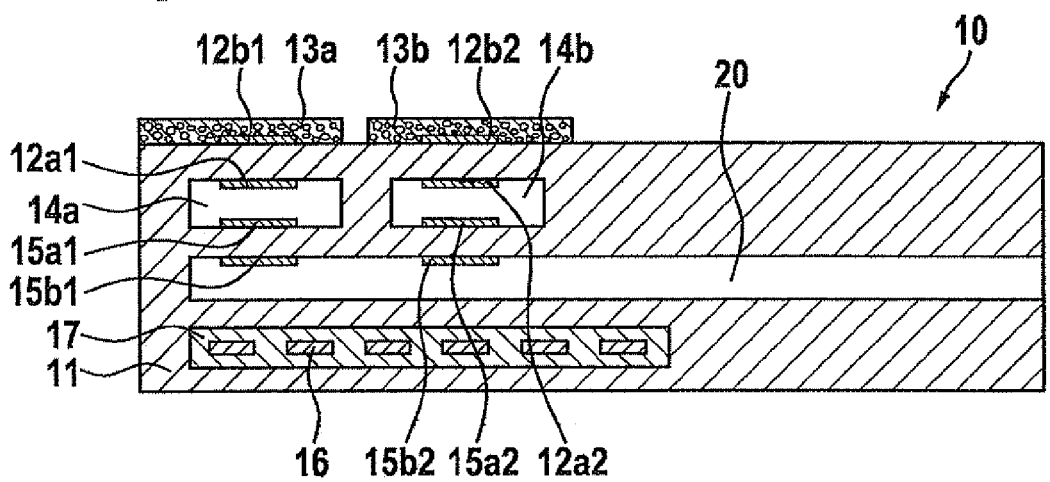
FIG. 3 shows a schematic longitudinal section of a sensor element according to a first variant of the sensor element depicted in FIG. 1.

FIG. 3 depicts a variant of the sensor element according to the first specific embodiment shown in FIG. 1. The same reference numerals designate the same components as in FIGS. 1 and 2.

The sensor element shown in FIG. 3 includes a first and a second interior chamber 14a, 14b, which are positioned for example in the same layer level of ceramic body 11 of sensor element 10, which is formed of ceramic layers. Positioned in each of these is a first internal pump electrode 12a1, 12a2 and a second internal pump electrode 15a1, 15a2. In this case first internal pump electrodes 12a1, 12a2, together with external pump electrodes 12b1, 12b2 placed on the large surface of the sensor element, form first electrochemical pump cells. External pump electrodes 12b1, 12b2 may be protected for example by porous protective layers 13a, 13b from the abrasive influence of the gas mixture which is to be detected.

In addition, internal pump electrodes 15a1, 15b2 together with external pump electrodes 15b1, 15b2 form second electrochemical pump cells. Sensor element 10 depicted in FIG. 3 thus includes two symmetrically formed sensitive areas which are used for determining gas components in the gas mixture to be detected.

If first external pump electrodes 12b1, 12b2 are implemented using different electrode materials, the associated first electrochemical pump cells may be utilized selectively to determine selected gas components of the gas mixture. For example, if the one first external pump electrode 12b1 is implemented as a catalytically inactive electrode or as a mixed potential electrode but the other first external pump electrode 12b2 is implemented as a catalytically active electrode, for example of platinum, then at the one first electrochemical pump cell 12a1, 12b1 almost exclusively the free oxygen of the gas mixture to be detected is transported electrochemically into first interior chamber 14a. In contrast, the sum of free oxygen contained in the gas mixture to be detected and of the oxygen resulting from the decomposition of the gas component to be detected is transported to the electrodes of the other first electrochemical pump cell 12a2, 12b2.

If the difference of the quantities of oxygen accumulated in first interior chambers 14a, 14b during the accumulation phase is then determined, the difference is a measure of the content of gas component to be detected in the gas mixture.

In order to obtain generally identical oxygen content in both interior chambers 14a, 14b at the beginning of the accumulation phase, first internal pump electrodes 12a1, 12a2 may be connected together to form an additional electrochemical pump cell, whereby equalization of the oxygen content in the two interior chambers 14a, 14b is achieved. During a measuring phase, the content of accumulated oxygen in interior chambers 14a, 14b may be determined using the particular second electrochemical pump cell 15a1, 15b1 or 15a2, 15b2 in the manner already described.

Another possibility is to connect first internal pump electrodes 12a1, 12a2 to second internal pump electrodes 15a1, 15a2, respectively, to form an electrochemical pump cell each, and to use the difference in concentration between the two interior chambers 14a, 14b to determine the oxygen content.

According to a third variant, first internal pump electrodes 15a1, 15a2 are connected to second internal pump electrodes 15b1, 15b2, respectively, to form electrochemical Nernst cells, and a determination of the oxygen concentration in first interior chambers 14a, 14b is performed on the basis of the occurring potential differences. Since oxygen is accumulated in first interior chamber 14a in a quantity which corresponds substantially to the quantity of free oxygen contained in the gas mixture, and in second interior chamber 14b a quantity of oxygen which corresponds to the sum of free oxygen contained in the gas mixture and the oxygen resulting from the decomposition of the gas component to be detected is accumulated, the determination of the difference in oxygen concentrations results directly in a measuring signal which corresponds substantially to the quantity of gas component to be detected.

Figure 4:
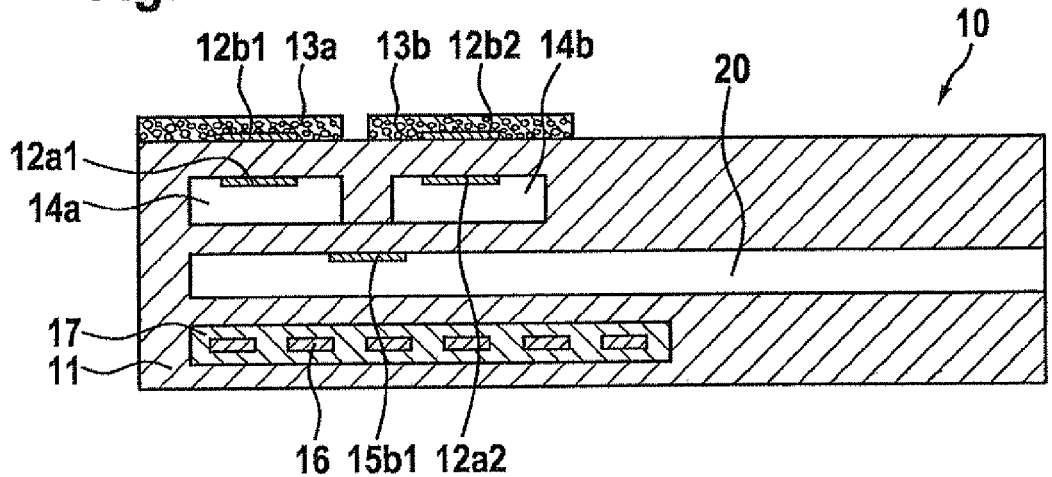
FIG. 4 shows a schematic longitudinal section of a sensor element according to a second variant of the sensor element depicted in FIG. 1.

FIG. 4 depicts another variant of the sensor element shown in FIG. 1 according to a first specific embodiment of the present invention. The same reference numerals continue to designate the same components as in FIGS. 1 through 3.

Since placing electrodes inside of ceramic sensor elements represents a certain cost factor, FIG. 4 shows a variant of the sensor element according to the first specific embodiment, whose construction is greatly simplified without a loss of function. While the construction of ceramic body 11 of sensor element 10 corresponds substantially to that depicted in FIG. 3, the number of electrodes needed is significantly reduced.

For example, in the sensor element depicted in FIG. 4, one of the second electrochemical pump cells is formed by one first pump electrode 12a1 together with second external pump electrode 15b1, and the other second electrochemical pump cell is formed by first internal pump electrode 12a2 together with shared second external electrode 15b1. Due to this sensor construction, second internal pump electrodes 15a1, 15a2 and one of the second external pump electrodes 15b2 may be dispensed with. This simplifies the construction of the sensor element significantly.

Another possibility for simplification, in the case of the sensor element shown in FIG. 3, is to short-circuit the connections of the one internal pump electrode 12a1, 15a1 or of the other internal pump electrode 12a2, 15a2 inside the sensor element to simplify the contacting. The same may apply to second external pump electrodes 15b1, 15b2. These electrodes may be short-circuited either inside the sensor element or in a plug which contacts the sensor element, in a supply line which connects the plug for example to a control unit, or inside a control unit. In addition, the function of electrodes 15b1 and 15b2, or of 12a1 and 15a1, or of 12a2 and 15a2 may be consolidated in each case in one electrode.

Figure 5:
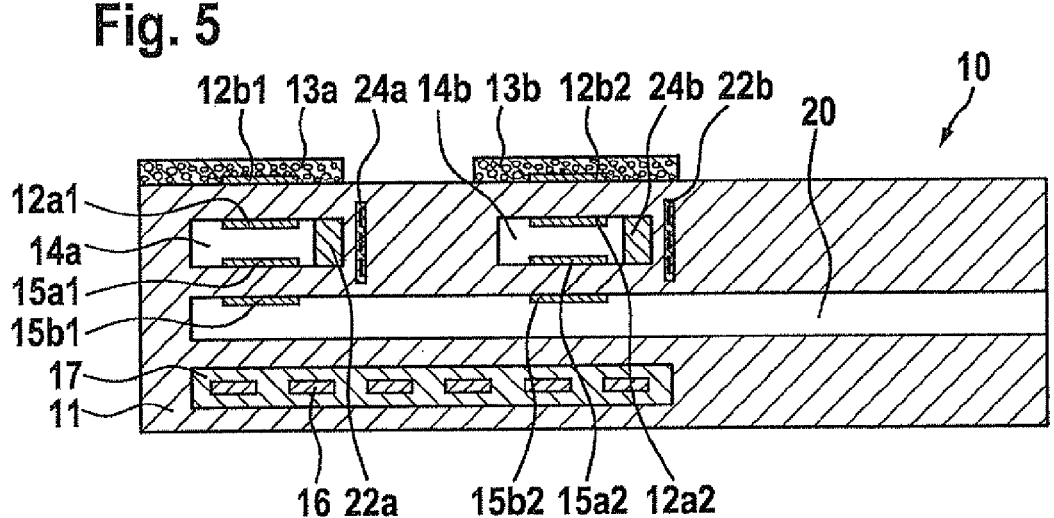
FIG. 5 shows a schematic longitudinal section of a sensor element according to a third variant of the sensor element depicted in FIG. 1.

FIG. 5 depicts a third variant of the sensor element shown in FIG. 1 according to a first specific embodiment of the present invention. The same reference numerals continue to designate the same components as in FIGS. 1 through 4.

The sensor element shown in FIG. 5 according to a third embodiment variant of the sensor element corresponds in large part to the sensor element shown in FIG. 3. In addition, however, preferably in at least one of interior chambers 14a, 14b a layer of an oxygen-absorbing or oxygen-storing or ceramic material is provided. This layer of an oxygen-storing material 22a, 22b is made for example of an oxygen storage material such as that used for example in NOx catalytic converters. Examples of oxygen-storing materials provided include ceramics containing zeolite, perovskite, or noble metal oxides such as palladium oxides.

An advantage of this system is that an overpressure of pumped-in oxygen does not occur in interior chambers 14a, 14b in the accumulation phase, since with increasing oxygen content increased storage of the pumped-in oxygen in the oxygen storing material of layers 22a, 22b occurs. In order to be able to determine the total content of oxygen contained in interior chambers 14a, 14b and in layers 22a, 22b during the subsequent measuring phase, sensor element 10 also has, for example, additional heating elements 24a, 24b, with the aid of which layers 22a, 22b of the oxygen-storing material may be warmed separately during the measuring phase, so that desorption of the stored oxygen occurs.

In this case the temperature, which is ensured by heating elements 24a, 24b, may be separately and specifically chosen and set depending on the choice of oxygen-storing material. Heating elements 24a, 24b are preferably designed in a form comparable to that of heating element 16, and are preferably in the area of layers 22a, 22b of an oxygen-storing material.

Figure 6:
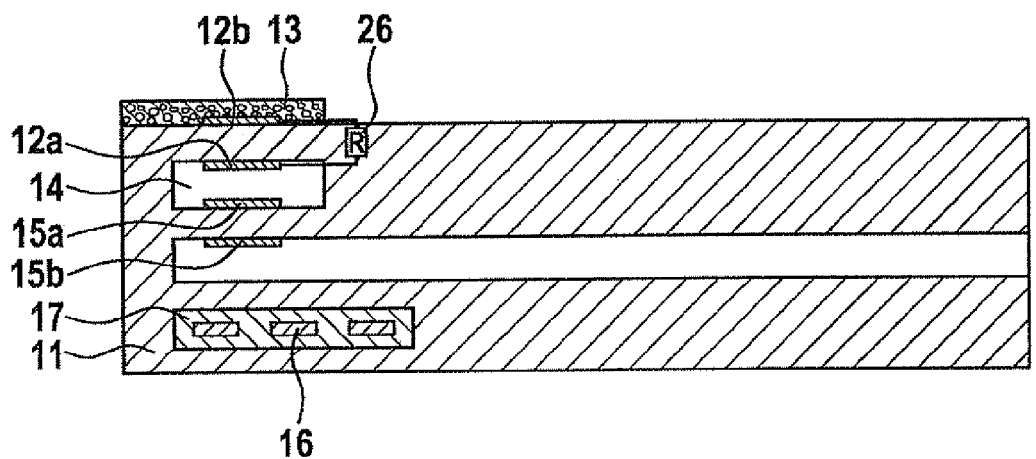
FIG. 6 shows a schematic longitudinal section of a sensor element according to a fourth variant of the sensor element depicted in FIG. 1.

FIG. 6 depicts a fourth variant of the sensor element shown in FIG. 1 according to a first specific embodiment of the present invention. The same reference numerals continue to designate the same components as in FIGS. 1 through 5.

In the sensor element shown in FIG. 6, first electrochemical pump cell 12a, 12b is designed as a so-called passive or autonomous pump cell. The manner of functioning of an autonomous electrochemical pump cell is based on the principle that it does not have a pump voltage applied to it, for example via an external connection, but rather that the electrodes of this electrochemical pump cell are short-circuited, for example through an ohmic resistor, and the pumping process which results at the pump electrodes of the autonomous pump cell occurs solely on the basis of concentration differences of the gas mixtures applied to the individual pump electrodes of the electrochemical pump cell.

In the present exemplary embodiment, first internal pump electrode 12a, which is exposed to the gas atmosphere in gas-tight sealed interior chamber 14, is short-circuited through an ohmic resistor 26 to first external electrode 12b, which is exposed to the gas mixture which is to be determined. Because of the oxygen partial pressure difference between the gas mixture to be determined and the gas atmosphere which prevails in first interior chamber 14, an electrochemical oxygen pumping process occurs, preferably in the direction of interior chamber 14. In this case ohmic resistor 26 is either integrated into ceramic body 11 or, as shown in FIG. 7, is positioned on a large surface of the sensor element, preferably on the same large surface on which first external pump electrode 12h is also located.

The last-named specific embodiment allows ohmic resistor 26 to be designed in the form of a trimmable resistor. Here ohmic resistor 26 is designed in the form of two resistor printed conductors, which are bridged by a plurality of electrically conductive jumpers 27a, 27b . . . If jumpers 27a, 27b . . . are severed in a suitable manner, so that only one of jumpers 27a, 27b, . . . results in a short-circuit of the resistor paths which form ohmic resistor 26, the length of the resulting total resistor path may be chosen appropriately and the electrical resistance of ohmic resistor 26 set thereby.

Also depicted in FIG. 7 are contact surfaces 29a, 29b for contacting electrodes of the sensor element, which are contacted to the corresponding sensor electrodes via contacts 30a, 30b and supply paths (not shown). The contacting of first internal pump electrode 12a with ohmic resistor 26 is accomplished via another through contact 30c.

A schematic representation of the wiring of the sensor element shown in FIGS. 6 and 7 is depicted in FIG. 8. The same reference numerals continue to designate the same components as in FIGS. 1 through 7.

Also depicted at the upper left of FIG. 8 is a sectional view of a sensor element which corresponds to a variant of the sensor element shown in FIG. 6. In the sensor element shown in FIG. 8, reference gas channel 20 is not situated in a separate layer level of ceramic sensor body 11, but preferably in the same layer level as interior chamber 14. This simplifies the construction of ceramic body 11, since one or more ceramic layers may be omitted.

The pump electrodes of second electrochemical pump cell 15a, 15h are preferably placed in this case on the walls of the ceramic partition which separates interior chamber 14 from reference gas channel 20. A contacting component 32 for contacting heating element 16 is also shown in this sectional view. In addition, a layer of an oxygen-absorbing material 22 is positioned in interior chamber 14.

FIG. 8 also shows at the lower left a top view of the sensor element according to the variant shown in FIG. 8, as well as an associated operating and analysis circuit at the right side. This includes a heater regulator 40, a control unit 42 for time-controlled, current-controlled, charge-controlled or voltage-controlled switching between various measuring or accumulation modes, a voltage source $U_i$, a current source $I_i$, an instrument for voltage measurement $U_m$ and an instrument for current measurement $I_m$, and preferably load resistors RI. An analysis circuit 44 is also provided.

FIG. 9 depicts a sensor element according to a second specific embodiment of the present invention. The same reference numerals continue to designate the same components as in FIGS. 1 through 8.

The sensor element shown in FIG. 9 has a simplified design, since incorporation of a separate reference gas channel is dispensed with. In this case the external pump electrode of second electrochemical pump cell 15b is not exposed to an air reference atmosphere, but rather preferably to the gas mixture which is to be detected. For this purpose, second external pump electrode 12b is situated for example on the same large surface of sensor element 10 on which first external pump electrode 12b is also located.

Figure 10:
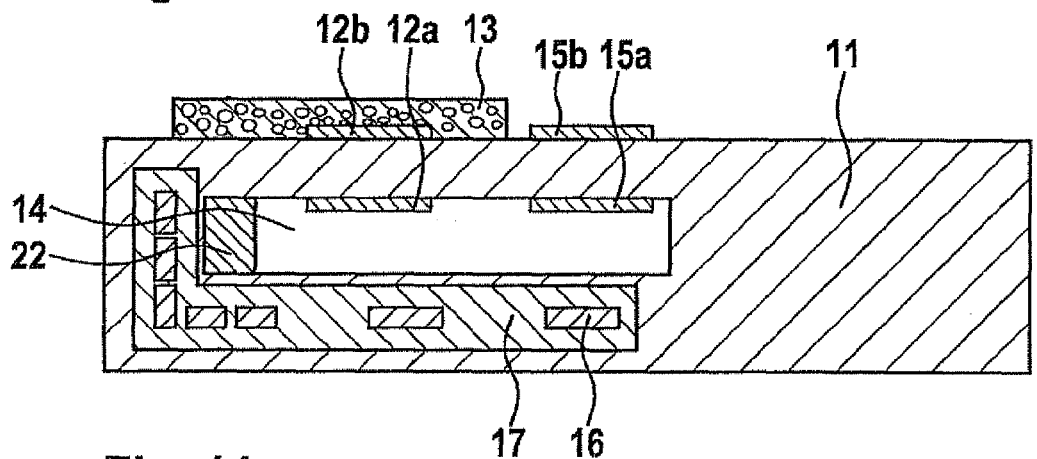
FIG. 10 shows a schematic longitudinal section of a sensor element according to a first variant of the sensor element depicted in FIG. 9.

A variant of the sensor element shown in FIG. 9 is depicted in FIG. 10. In the latter case, heating element 16 is implemented in an asymmetrical variant. To enable intensive heating of layer 22 of an oxygen-storing material provided in interior chamber 14, in this area heating element 16 is equipped with a higher heating power. This may be achieved either through a greater spatial density of resistor printed conductors per unit of area, or a resistor printed conductor with a greater electrical resistance is provided. In this way, the warming of oxygen-absorbing layer 22 needed for desorption in the measuring phase can be guaranteed.

Figure 11:
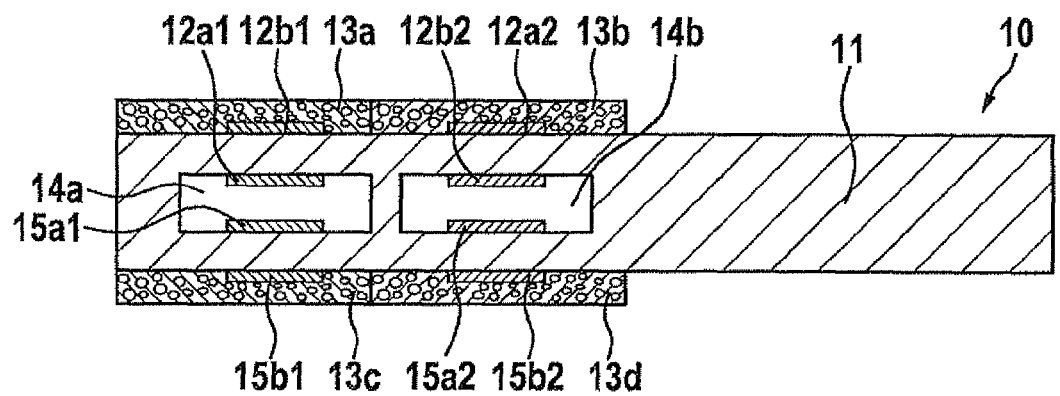
FIG. 11 shows a schematic longitudinal section of a sensor element according to a second variant of the sensor element depicted in FIG. 9.

FIG. 11 depicts a sensor element according to a third specific embodiment of the present invention. The same reference numerals continue to designate the same components as in FIGS. 1 through 10.

The sensor element depicted in FIG. 11 also shows a simplified design, since the incorporation of a reference gas channel 20 into ceramic body 11 of the sensor element is dispensed with. Sensor element 10 includes essentially four largely identical or symmetrically designed electrochemical pump cells 12$a$1, 12$b$1; 12$a$2, 12$b$2; 15$a$1, 15$b$1 and 15$a$2, 15$b$2. In this case each of the external pump electrodes 12$b$1, 12$b$2, 15$b$1 and 15$b$2 is preferably protected by porous protective layers 13$a$, 13$b$, 13$c$, 13$d$ against abrasive influences of the gas mixture to be detected.

Figure 12:
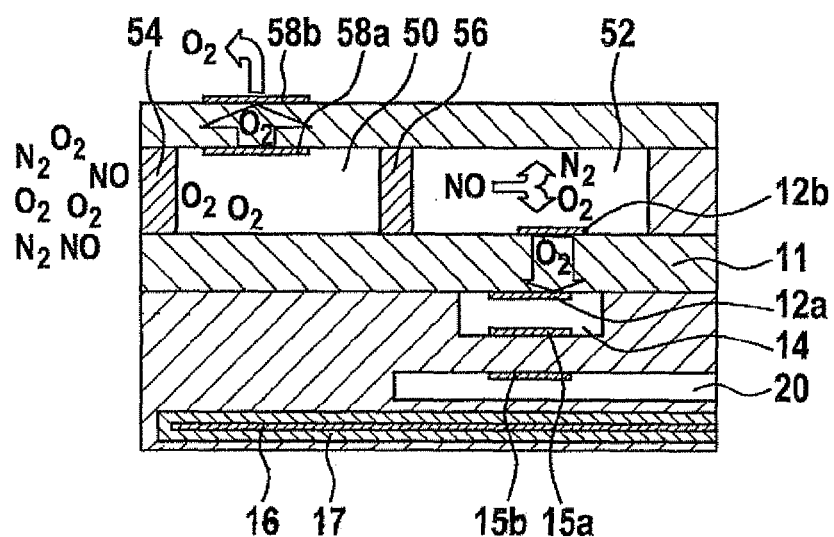
FIG. 12 shows a schematic longitudinal section of a sensor element according to a third specific embodiment of the present invention.

FIG. 12 shows a sensor element according to another specific embodiment of the present invention. Here too, the same reference numerals designate the same components as in FIGS. 1 through 11. Additional variants of this specific embodiment may be found in FIGS. 13 through 17.

The design of the sensor element shown in FIG. 12 is based on the principle that before the gas mixture to be detected comes into contact with electrochemical pump cells of the sensor element which are used for accumulating oxygen in a separate gas-tight sealed interior chamber 14, it is subjected to a process upstream in the flow direction, preferably within sensor element 10, for reducing the content of free oxygen in the gas mixture to be detected.

To that end, sensor element 10 according to FIG. 12 has a first measuring gas chamber 50 and a second measuring gas chamber 52. First measuring gas chamber 50 here is separated from a gas mixture to be detected which surrounds the sensor element, by a first diffusion barrier 54, which is made for example of a porous ceramic material, and second measuring gas chamber 52 is separated from first measuring gas chamber 50 preferably by a second diffusion barrier 56, which may also be made of a ceramic porous material.

Inside first measuring gas chamber 50 is preferably a fourth internal pump electrode 58$a$, which forms an electrochemical pump cell together with a fourth external pump electrode 58$b$ which is placed on the large surface of the sensor element. Fourth electrochemical pump electrode 58$a$, 58$b$ serves to remove free oxygen from the gas mixture to be detected, which is diffusing into first measuring gas chamber 50, largely without the gas component to be detected of the gas mixture to be determined being decomposed in the process.

For this purpose, fourth internal pump electrode 58$a$ is made for example of a selectively catalytically active material, which releases in particular free oxygen electrochemically, but leaves other oxidizable or reducible components of the gas mixture substantially unchanged. Alternatively, the selectively catalytically active material is designed in such a way that it preferably allows all the other gas components contained in a gas mixture which is to be determined to react, except for the one which is to be determined. A gold or platinum-gold electrode, for example, is suitable for this.

The gas mixture to be detected, which has been at least partially freed of free oxygen in this way, passes through second diffusion barrier 56 into second interior gas chamber 52, in which first external pump electrode 12$b$ is placed. Together with first internal pump electrode 12$a$, this causes an electrochemical transport process of oxygen resulting from the decomposition of the gas component to be detected, into interior chamber 14. The mode of operation of the sensor element shown in FIG. 12, based on an accumulation and measuring phase, subsequently runs generally similarly to that described for the previous exemplary embodiments.

Figure 13:
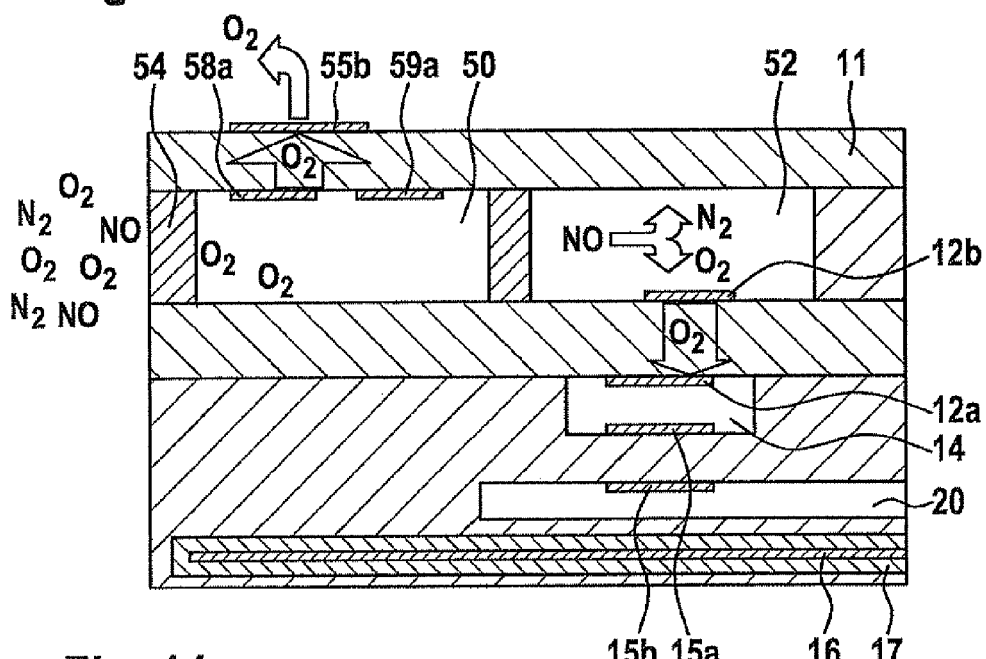
FIG. 13 shows a longitudinal section of a sensor element according to a first variant of the sensor element depicted in FIG. 12.

According to the variant shown in FIG. 13 of the sensor element depicted in FIG. 12, within measuring gas chamber 50, along with fourth internal pump electrode 58$a$, a fifth internal pump electrode 59$a$ is placed. Here fourth internal pump electrode 58$a$ together with fourth external pump electrode 58$b$ forms a fourth electrochemical pump cell, and fifth internal pump electrode 59$a$ together with fourth external pump electrode 58$b$ forms a fifth electrochemical pump cell.

During operation, the potential applied to fourth and fifth electrochemical pump cells 58$a$, 58$b$ and 59$a$, 58$b$ is chosen in such a way that a large part of the free oxygen available in the gas mixture is electrochemically removed at internal pump electrode 58$a$ of fourth electrochemical pump cell 58$a$, 58$b$, and a residual content of free available oxygen is electrochemically removed at fifth internal pump electrode 59$a$ due to the lower potential of the latter. In both cases, electrochemical decomposition of the gas component to be detected in the gas mixture at internal pump electrodes 58$a$, 59$a$ is avoided.

Figure 14:
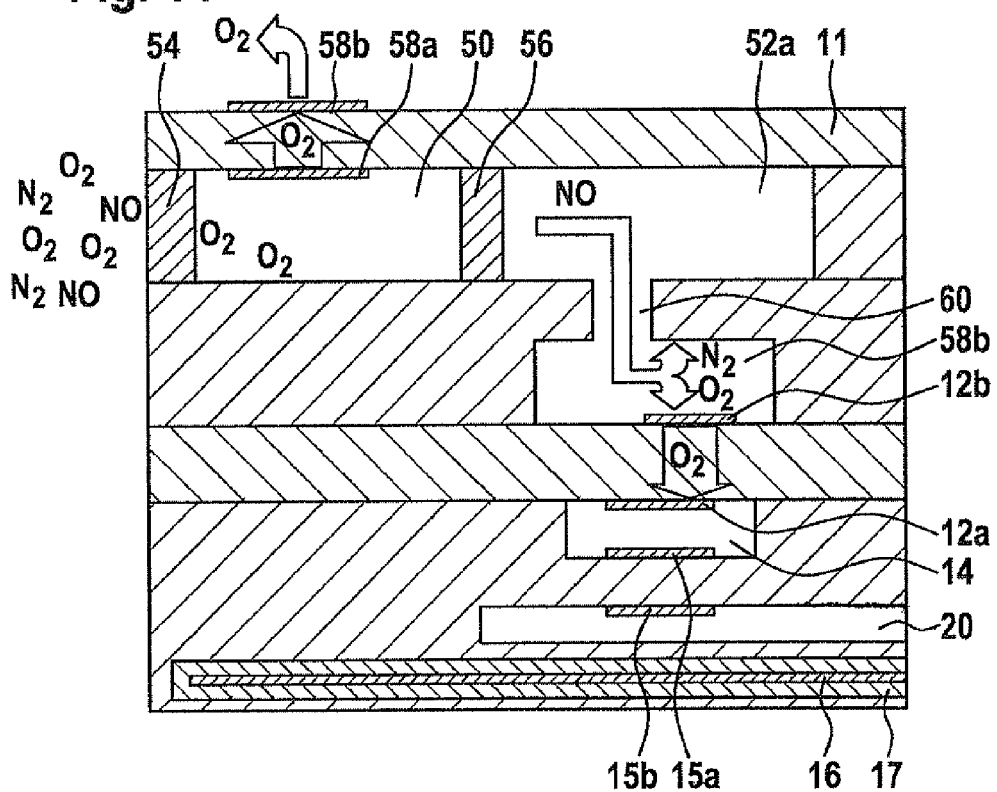
FIG. 14 shows a schematic longitudinal section of a sensor element according to a second variant of the sensor element depicted in FIG. 12.

FIG. 14 shows another variant of the sensor element depicted in FIG. 12. In this variant, second measuring gas chamber 52 is divided into a first compartment 52$a$ and a second compartment 52$b$, which is preferably located in a different layer level. Between compartments 52$a$, 52$b$ there is another diffusion barrier, for example in the form of a bore hole 60 through a ceramic layer of sensor body 11. The advantage of this system is the spatial separation of the electrochemical cells, and due to the placement in different layer levels of the sensor element, effective limitation of possible mutual contamination of the associated electrodes.

Figure 15:
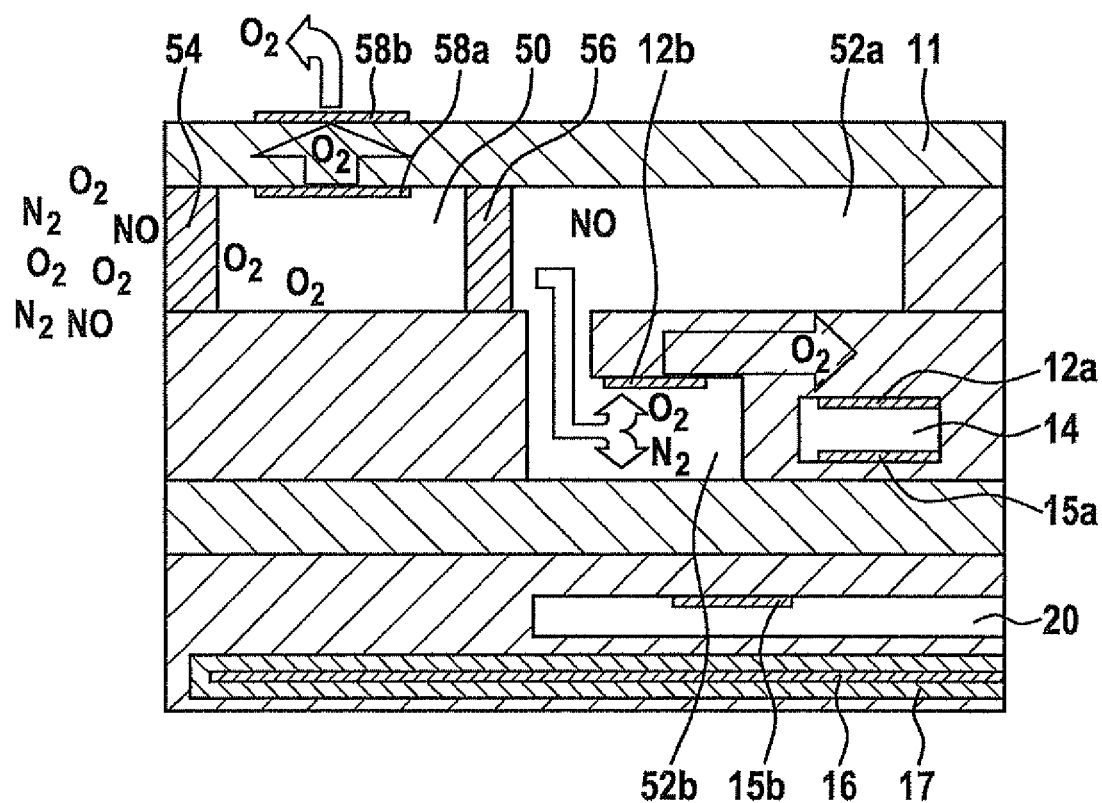
FIG. 15 shows a schematic longitudinal section of a sensor element according to a third variant of the sensor element depicted in FIG. 12.

FIG. 15 shows a third variant of the sensor element depicted in FIG. 12. The variant depicted corresponds largely to that in FIG. 14, except that second compartment 52$b$ is generally in the same ceramic layer level as interior chamber 14. This results in a simplified construction, compared to that depicted in FIG. 14.

Figure 16:
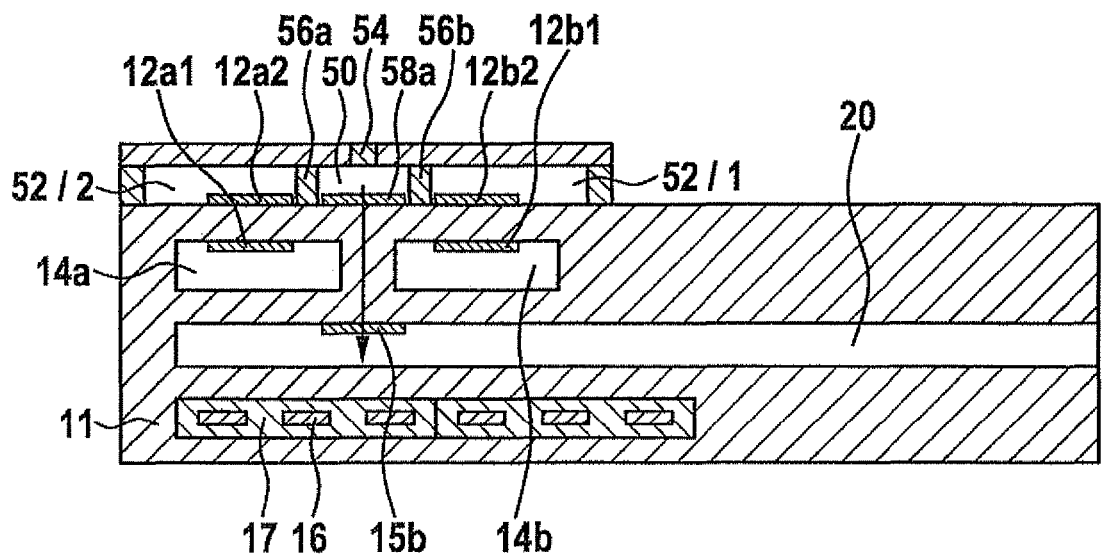
FIG. 16 shows a schematic longitudinal section of a sensor element according to a fourth variant of the sensor element depicted in FIG. 12.

FIG. 16 shows a fourth variant of the sensor element depicted in FIG. 12. This specific embodiment represents a mixture of the variants shown in FIG. 12 and in FIG. 14.

The sensor element shown in FIG. 16 includes a first measuring gas chamber 50, which is in fluid-conducting contact with two second measuring gas chambers 52/1 and 52/2 through two gas diffusion barriers 56$a$, 56$b$. First measuring gas chamber 50 is in contact with the gas mixture to be detected, for example via a hole bored in the upper boundary surface of first measuring gas chamber 50, which is filled with a diffusion barrier 54 made of a porous ceramic material. At the same time, fourth internal pump electrode 58$a$ forms an electrochemical pump cell, preferably with second external pump electrode 15$b$ situated in reference gas channel 20, to remove the free molecular oxygen which diffuses into first measuring gas chamber 50. This direction of transport is clarified by an arrow in FIG. 16.

The gas mixture, largely freed of molecular oxygen, then diffuses through second diffusion barriers 56$a$, 56$b$ into second internal gas chambers 52/1 and 52/2. The accumulation of a quantity of oxygen in interior gas chambers 14$a$, 14$b$ equivalent to the gas component to be detected proceeds in a manner similar to that described earlier.

Figure 17:
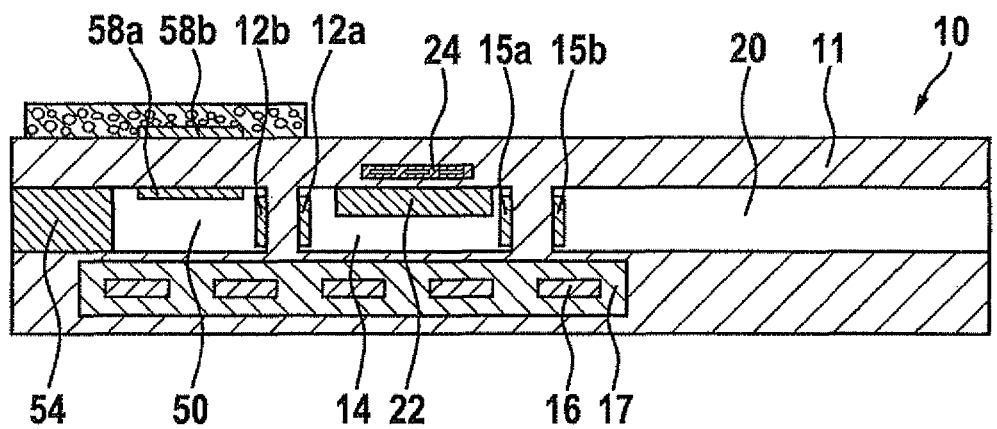
FIG. 17 shows a schematic longitudinal section of a sensor element according to a fourth specific embodiment of the present invention.

FIG. 17 shows a fifth variant of the sensor element depicted in FIG. 12. This sensor element has a particularly simple construction, since all interior gas chambers of the sensor element are situated in generally the same layer level of ceramic body 11. In this way, a cost-saving sensor element is achievable. Interior chamber 14 is separated from first measuring gas chamber 50, for example by a ceramic boundary surface, the electrodes of first electrochemical pump cell 12a, 12b preferably being located on this boundary surface.

Interior chamber 14 continues to be separated from reference gas channel 20 by a second ceramic boundary surface, the electrodes of second electrochemical pump cell 15a, 15b preferably being located on this second ceramic boundary surface. The manner of functioning of this variant is based essentially on that already described previously.

The described sensor elements serve in particular to show the presence of or to determine the concentration of gas components of a gas mixture which are reducible, and which thus release oxygen, for example when they are decomposed electrochemically. These are, for example, nitrogen or sulfur oxides or carbon dioxide.

Similarly, the described sensor elements may, however, also be used to show the presence of oxidizable gas components such as ammonia, hydrocarbons, carbon monoxide or hydrogen. In this case an inverse pump voltage is applied to the electrodes of first electrochemical pump cell 12a, 12a1, 12a2, 12b, 12b1, 12b2 in the accumulation phase, so that oxygen is transported out of interior chamber 14, 14a, 14b to oxidize the oxidizable gas components which are to be detected. The oxygen deficit which develops thereby in interior chamber 14, 14a, 14b is used subsequently as a signal proportional to the concentration of gas component to be detected.

The described sensor elements are used for determining gas components, for example in exhaust gases from internal combustion engines, power plants, or home furnace systems. They may be used for example in exhaust pipes of internal combustion engines to monitor the functioning of three-way catalytic converters, nitrogen oxide storage catalytic converters or diesel particle filters.

What is claimed is:

1. A sensor element of a gas sensor for determining gas components in an exhaust gas of an internal combustion engine, comprising:
    a ceramic sensor body having at least one interior chamber which is sealed in a gas-tight manner, in which at least one first internal electrode is positioned, wherein the chamber is not in fluid-conducting contact with the exhaust gas;
    a second electrode, which, together with the first electrode in the chamber forms a first electrochemical cell; and
    an additional electrode, which, together with the first electrode in the chamber forms a second electrochemical cell;
    wherein the first electrochemical cell is an electrochemical pump cell and the additional electrode is exposed to a gas being measured.

2. The sensor element as recited in claim 1, wherein both the first and second electrochemical cells are electrochemical pump cells, to whose electrodes a pump voltage is applied, at least in phases.

3. The sensor element as recited in claim 1, wherein the first and second electrodes are connected to each other through a trimmable resistor.

4. The sensor element as recited in one of claim 1, wherein at least one of the second and the additional electrode is a mixed-potential electrode.

5. The sensor element as recited in claim 1, wherein a layer of an oxygen-storing material is provided in the interior chamber.

6. The sensor element as recited in claim 5, further comprising:
    two heating elements to heat the sensor element, one of the heating elements being positioned in an area of the layer of oxygen-storing material, such that the layer of the oxygen-storing material is warmed to a temperature which differs from that of remaining compartments of the sensor element.

7. The sensor element as recited in claim 5, wherein the sensor body has an additional interior gas chamber which is in fluid-conducting contact with the exhaust gas, the gas chamber having an electrode which selectively catalytically decomposes molecular oxygen contained in the exhaust gas.

8. A method for determining gas components in an exhaust gas of an internal combustion engine using a sensor element having at least two electrochemical pump cells which each include at least one first electrode and one second electrode, at least one of the electrodes being positioned in a gas-tight sealed interior chamber of the sensor element, the method comprising:
    accumulating a quantity of oxygen in the gas-tight sealed interior chamber equivalent to a quantity of a gas component to be determined, wherein the chamber is not in fluid-conducting contact with the exhaust gas;
    subsequently removing the accumulated oxygen by applying a pump voltage to the electrodes of at least one of the electrochemical pump cells; and
    determining the gas components based on an electrical characteristic of the at least one of the electrochemical pump cells as the removing is performed.

9. The method as recited in claim 8, wherein during the removal of the accumulated oxygen applying a pump voltage to the electrodes of both electrochemical pump cells, the pump voltage applied to a first of the at least two electrochemical cells differing in level from the pump voltage applied to a second of the at least two electrochemical pump cells.

10. The method as recited in claim 9, wherein during the removal of the accumulated oxygen a constant pump voltage is applied to the at least one first electrode, relative to an additional electrode which is exposed to a reference gas atmosphere.

11. The method as recited in claim 9 wherein during the removal of the accumulated oxygen a constant pump voltage is applied to the at least one first electrode, relative to an additional electrode which is exposed to the exhaust gas.

12. A method of determining nitrogen oxide content in an exhaust gas using a sensor element having at least two electrochemical pump cells which each include at least one first electrode and one second electrode, at least one of the electrodes being positioned in a gas-tight sealed interior chamber of the sensor element, the method comprising:
    accumulating a quantity of oxygen in the gas-tight sealed interior chamber equivalent to a quantity of the nitrogen oxide content to be determined;
    subsequently removing the accumulated oxygen by applying a pump voltage to the electrodes of at least one of the electrochemical pump cells; and
    determining the quantity of the nitrogen oxide content based on an electrical characteristic of the at least one of the electrochemical pump cells as the removing is performed.

13. A method of monitoring a functional reliability of an NOx catalytic converter using a sensor element having at least two electrochemical pump cells which each include at least one first electrode and one second electrode, at least one of the electrodes being positioned in a gas-tight sealed interior chamber of the sensor element, the method comprising:
- accumulating a quantity of oxygen in the gas-tight sealed interior chamber equivalent to a quantity of a gas component to be determined, wherein the chamber is not in fluid-conducting contact with an exhaust gas;
- subsequently removing the accumulated oxygen by applying a pump voltage to the electrodes of at least one of the electrochemical pump cells; and
- monitoring the functional reliability of the $NO_x$ catalytic converter based on an electrical characteristic of the at least one of the electrochemical pump cells as the removing is performed.

14. A method of monitoring an SCR exhaust treatment system using a sensor element having at least two electrochemical pump cells which each include at least one first electrode and one second electrode, at least one of the electrodes being positioned in a gas-tight sealed interior chamber of the sensor element, the method comprising:
- accumulating a quantity of oxygen in the gas-tight sealed interior chamber equivalent to a quantity of a gas component to be determined, wherein the chamber is not in fluid-conducting contact with an exhaust gas; and
- subsequently removing the accumulated oxygen by applying a pump voltage to the electrodes of at least one of the electrochemical pump cells; and
- monitoring the SCR exhaust treatment system based on an electrical characteristic of the at least one of the electrochemical pump cells as the removing is performed.

* * * * *